(12) United States Patent
Suba

(10) Patent No.: US 7,802,900 B2
(45) Date of Patent: Sep. 28, 2010

(54) LIGHT REFLEX TESTING DEVICE

(76) Inventor: Sebastian S. Suba, 1400 Gateway Hills, #914, Ames, IA (US) 50014

( * ) Notice: Subject to any disclaimer, the term of this patent is extended or adjusted under 35 U.S.C. 154(b) by 354 days.

(21) Appl. No.: 11/980,863

(22) Filed: Oct. 30, 2007

(65) Prior Publication Data

US 2009/0109402 A1   Apr. 30, 2009

(51) Int. Cl.
*F21V 9/00* (2006.01)
(52) U.S. Cl. .................. 362/230; 362/227; 362/234; 362/552; 362/555; 362/572
(58) Field of Classification Search ............... 362/227, 362/230, 234, 253, 551, 552, 555, 572, 577; 351/221
See application file for complete search history.

(56) References Cited

U.S. PATENT DOCUMENTS

2004/0105075 A1\*   6/2004   Kandel et al. ............... 351/221

\* cited by examiner

*Primary Examiner*—Sandra L O'Shea
*Assistant Examiner*—Meghan K Dunwiddie
(74) *Attorney, Agent, or Firm*—Brett Trout

(57) ABSTRACT

A calorimetric pupil light reflex testing device for diagnostic assessment of the ocular and central nervous system diseases based on melanopsin and non-melanopsin spectral light properties. The device employs blue and red light emitting diodes emitting light at wavelengths of approximately 472 nanometers and 630 respectively to elicit pupillary constriction. The light emitting diodes are each provided within a handheld light wand, allowing the light emitting diodes to be hand held. The light emitting diodes provide intense light and the predetermined wavelengths, thereby eliminating the necessity of a light meter or colored filter.

18 Claims, 8 Drawing Sheets

LIGHT REFLEX TESTING DEVICE

BACKGROUND OF THE INVENTION

1. Field of the Invention

The present invention relates in general to an ocular diagnostic tool and, more particularly, to an colorimetric pupil light reflex testing device for diagnostic assessment of the ocular and central nervous system diseases based on melanopsin and non-melanopsin spectral light properties.

2. Description of the Prior Art

It is known in the art to diagnose various types of abnormalities in humans and animals using the reaction of a pupil to specific wavelengths of light. The pupil light reflex evaluation provides an objective method for assessing function of the retina and optic nerve. The pupil light reflex is driven by photoreceptor activity (rods and cones) and a subpopulation of retinal ganglion cells, which contain a photosensitive pigment called melanopsin. Physiological spectral properties of healthy retinas provide a baseline against which to use a calorimetric device for testing the pupil for both photoreceptor-mediated pupil light reflex and melanopsin-mediated pupil light reflex.

Melanopsin is a photosensitive pigment activated by a high light intensity (30 kcd/m2 or higher) with a peak spectral sensitivity in the blue (480+/−50 nm) range. Photoreceptor-mediated pupil light response is activated by different wave lengths, but the activation occurs at very low light intensities (25 cd/m2). Since red light (630 nm+/−40 nm) can activate photoreceptor-mediated pathways, the melanopsin mediated pupil light response can not be activated since spectral properties of the red light fall behind the melanopsin spectral sensitivity.

Diagnosis of ocular abnormalities based upon pupil-light reflex is known in the art. A pupil of an animal or human is exposed to a specified wavelength of blue light and then to a specified wavelength of red light. A veterinarian or doctor can then make various diagnoses based upon pupil-light reflex to exposure to the two wavelengths. However, in the past, making an ocular abnormality diagnosis based upon pupil-light reflex has been limited by the use of white light only for evaluation of the pupil light reflex which contains both red and blue wavelengths of light.

To obtain the required wavelengths of blue and red light, prior art systems combined white light with different color filters. The filters block out all of the light at undesired wavelengths, but will let pass the desired wavelength for which the filter was designed. The width of the pass band of wavelengths can be wide or narrow, based upon the filter type. In addition, prior art filters often "leak" light at undesired wavelengths, which can lead to an ambiguous or even incorrect diagnosis. Although there are filters which minimize leakage, such filters are typically quite expensive and hard to find in usable sizes. The efficiency of prior art filters is typically low. Prior art filters need to have a very narrow wavelength band pass (approx 3 nm), centered around 480 nm for blue light and around 630 nm for red light. This means that only about 1-3% of total light is passing through the filter.

An extremely powerful white light is necessary in order to have a decent light output after the filter. Such lights consume a significant amount of power, generate intense heat, are expensive and require expensive systems to operate effectively. Also, in time, the incandescent bulbs have a decrease in light output and need to be replaced after a specific hours of usage. Incandescent lamps dim as they age (projector lamps for example are rated for approximate 2000 hours and they cost $300-$600 or more to replace.) A filter with a wider wavelength band pass can be used in order to achieve a better transmittance and increase the efficiency, but at the cost of diagnostic precision. Additionally, given the large amount of light required and the reduction of light transmission associated with prior art filters, it is often necessary to provide an instrument to measure the light output in order to determine the precise luminance of the light irradiating the pupil (candela/square meter). Luminance is a photometric measure of the density of luminous intensity in a given direction. It describes the amount of light that passes through, or is emitted from, a particular area, and falls within a given solid angle. The luminance indicates how much luminous power will be perceived by an eye looking at the surface from a particular angle of view. Luminance is thus an indicator of how bright the surface will appear. In this case, the solid angle of interest is the solid angle subtended by the eye's pupil. Instruments capable of accurately measuring such luminous are often expensive and difficult to use.

The requirement of a large intensity light source, a specific wavelength filter and a luminance measuring instrument leads to a prior art process requiring a large amount of heavy, complicated and expensive instruments. It would be desirable, therefore, to provide a system for reducing the weight, cost, complexity and variability associated with such prior art systems.

Additionally, as such prior art systems typically require hot lights, filters and luminescence meters to be held at various times and at various locations, it is often difficult to conduct a diagnosis with a single individual. Even if a single individual could accomplish the diagnosis, the prior art process typically does not allow the user a free hand to manipulate the eyelid and/or a camera to record the results. It would, therefore, be desirable to provide a system which could be used by a single operator with a single hand.

Utilization of a filter in front of a light source typically leads to a certain amount of variability in the light source being transmitted. Even with a luminescence meter recording the light passing through the filter, the leakage of the filter combined with the movement of the filter by the user can lead to an indeterminate result. Therefore, it would be desirable to provide a method for diagnosing ocular abnormalities using pupil-light reflex, which is accurate and consistent.

Yet another drawback associated with the prior art is that given the variability and intensity of prior art machines, prior art machines sometimes require the user to increase the intensity beyond a desirable level to elicit the response necessary for the diagnosis. Increasing the light intensity beyond the desired diagnostic level, however, can lead to additional damage of the eye. Conversely, in situations where the power is decreased to avoid damage to the eye, the diagnosis often cannot be made, or the light is left on the pupil for an extended period of time in an effort to elicit the response, thereby again leading to the potential for damage to the eye associated with overexposure. It would, therefore, be desirable to provide a light source with a consistent output to decrease the likelihood of damage to the eye associated with the diagnosis.

SUMMARY OF THE INVENTION

In an advantage provided by this invention, a colorimetric pupil light reflex testing device is provided to allow diagnostic assessment ocular and central nervous system diseases.

Advantageously, this invention provides a calorimetric pupil light reflex testing device which is of a low cost and lightweight manufacture.

Advantageously, this invention provides a colorimetric pupil light reflex testing device which provides known consistent wavelengths of light.

Advantageously, this invention provides a colorimetric pupil light reflex testing device which provides light of a known consistent intensity.

Advantageously, this invention provides a colorimetric pupil light reflex testing device which is easy to maintain.

Advantageously, this invention provides a colorimetric pupil light reflex testing device which is portable.

Advantageously, this invention provides a colorimetric pupil light reflex testing device with separate light sources for both red and blue light.

Advantageously, this invention provides a colorimetric pupil light reflex testing device which focuses and then diffuses light to reduce power consumption requirements.

Advantageously, this invention provides a colorimetric pupil light reflex testing device which provides longer lasting light sources.

Advantageously, this invention provides a calorimetric pupil light reflex testing device which allows for quick and easy calibration.

In an embodiment of this invention, an illumination system is provided with a light pen. The light pen is provided with a light emitting diode source, producing at least 50 kcd/m$^2$ more light at 630 nanometers than at 480 nanometers. In the preferred embodiment, the system is also provided with a light emitting diode source producing at least 50 kcd/m$^2$ more light at 480 nanometers than 630 nanometers. Preferably, the light sources emit light at an intensity of around 200 kcd/m$^2$ and are used within 2.5 centimeters of an eye for five seconds to determine pupil constriction. The amount of pupil constriction associated with the red light and the blue light allows diagnosis of various medical abnormalities.

BRIEF DESCRIPTION OF THE DRAWINGS

The present invention will now be described, by way of example, with reference to the accompanying drawings in which.

DETAILED DESCRIPTION OF THE PREFERRED EMBODIMENT

Figure 1:
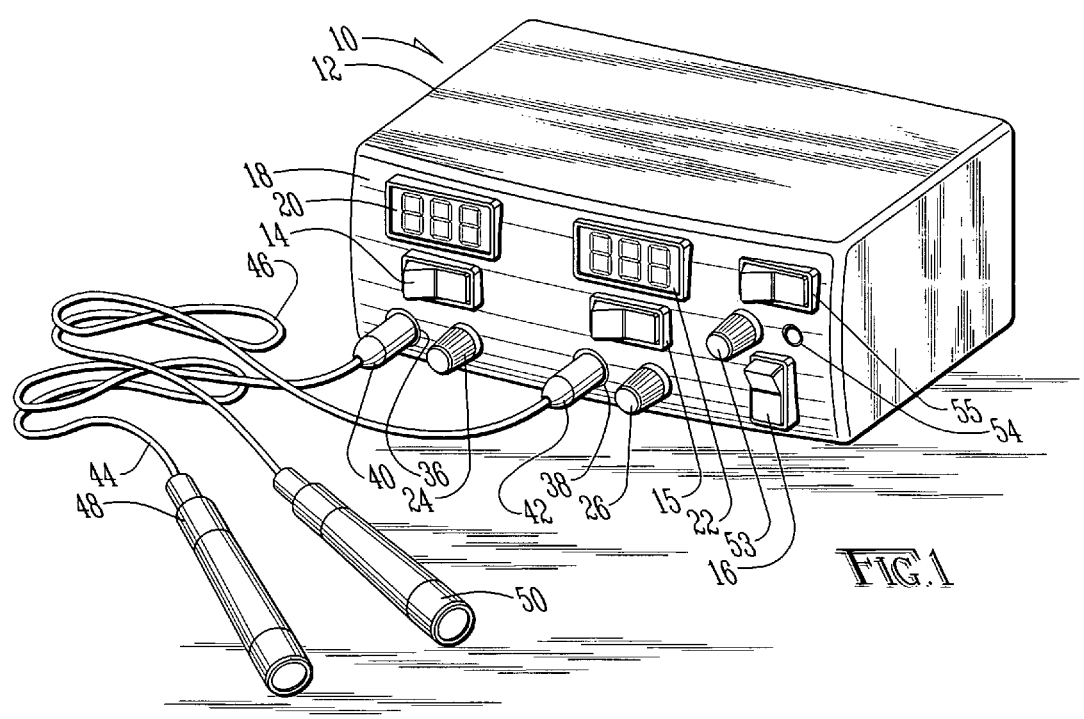
FIG. 1 illustrates a front perspective view of the diagnostic system of the present invention.

With reference to the drawings, a colorimetric pupil light reflect testing device is shown generally as (10) in FIG. 1. The device (10) includes a housing (12) which may be constructed of plastic or any suitable material. The housing (12) and all of its internal components preferably weighs less than 10 kilograms and, more preferably less than 5 kilograms. The device (10) includes three rocker switches (14), (15) and (16) which may be of any suitable on/off type known in the art. Provided on the face (18) of the housing (12) are two three and a half digit liquid crystal display (LCD)/voltmeters (20) and (22). The displays may alternatively be light emitting diode displays or any other desired type of display. Provided below the displays (20) and (22) are two potentiometer knobs, (24) and (26).

Also provided on the housing (12) are two outputs (36) and (38), coupled to a pair of jacks (40) and (42). The jacks (40) and (42) are coupled by power conduits (44) and (46) to a pair of light wands (48) and (50). While the power conduits (44) and (46) may be of any desired construction, in the preferred embodiment they are wires for the transmission of electricity from the housing (12) to the light wands (48) and (50). Additionally, the housing (12) is provided with a fiber optic outlet (54) for white light, if it is desired to use a device that has an input for fiber optic light guide in association with the diagnostic device (10). A potentiometer knob (53) and on/off switch (55) for the fiber optic outlet (54) are also provided on the face (18) of the housing (12).

Figure 2:
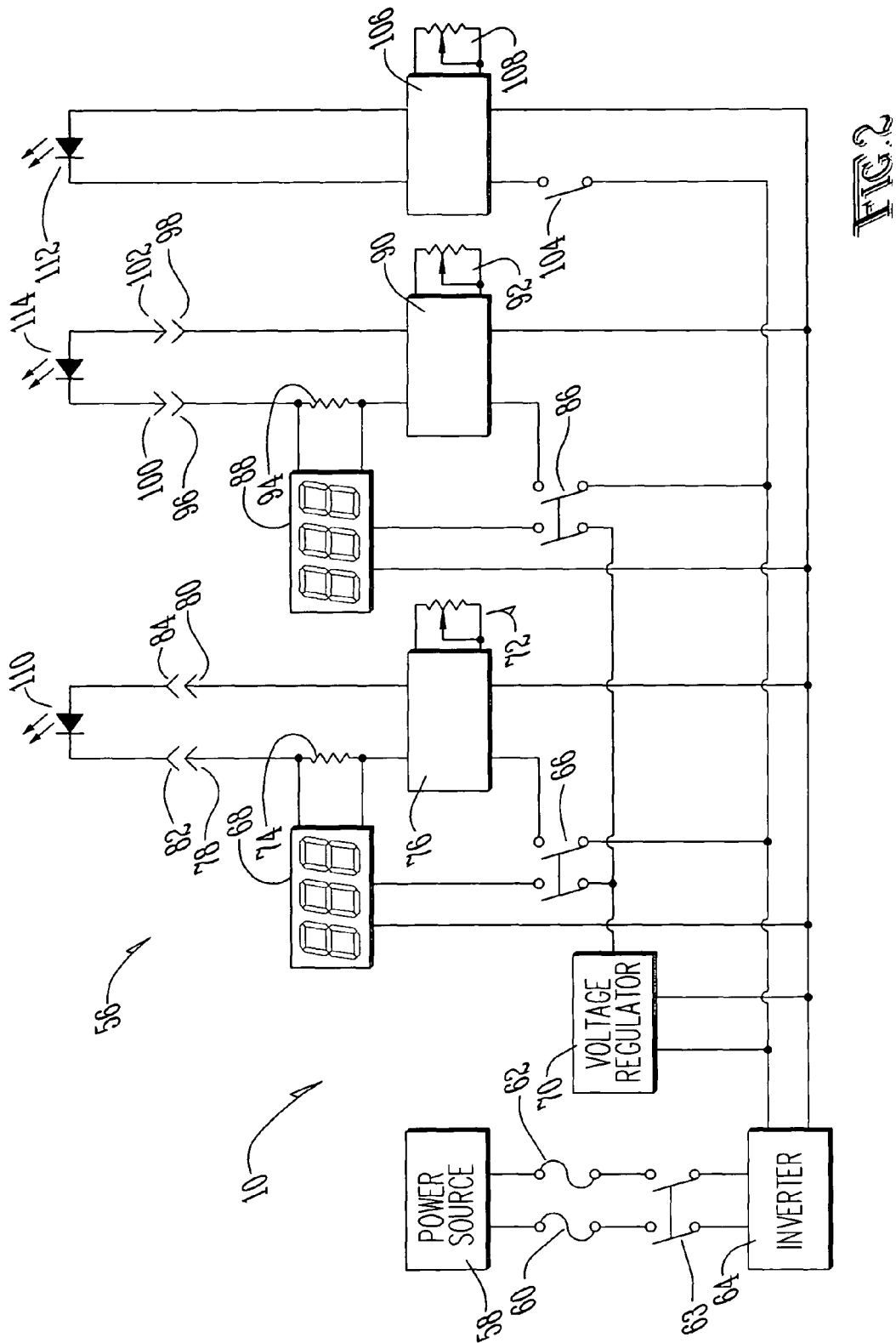
FIG. 2 illustrates a schematic of the electronic components and connections for the diagnostic system of FIG. 1.

Shown in FIG. 2 is a schematic (56) of the elements of the device (10). (FIGS. 1-2). As shown in FIG. 2, the diagnostic device (10) is provided with a connection to a power supply (58) such as an alternating current supply ranging from 110 volt to 220 volt. The connection may be a standard plug (not shown) or any other desired connection method. Coupled to the power supply (58) is a pair of 2.5 amp fast blow fuses (60) and (62), utilized to protect the electronics associated with the diagnostic device (10). The power supply (58) is coupled via a double on/off switch (63) to a medical grade, regulated output inverter (64), such as a Mean Well NPS-30-12, 12 volt DC 0~2.5 amp power supply. Coupled to the inverter (64) is a voltage regulator (70) which may be of any type known in the art to convert power coming from the power source (58) to the desired output which, in the preferred embodiment is five volts.

A double position on/off switch (66) controls power from the voltage regulator (70) to a three and one-half digit LCD/ voltmeter display (68), such as a ±200 mV DMS-20LCD digital panel voltmeter from Datel®. The switch (66) also controls power from the inverter (64) to a light emitting diode driver (76). While any type of driver maybe utilized, in the preferred embodiment, the driver (70) is a 700 mA Luxdrive model 03021-D-E-700, BuckPuck® Wide Range LED Power Module. Coupled to the driver (70) is a 1 kOhm potentiometer (72) to adjust the power, which in turns controls the light intensity. For measuring values greater than the full scale input of the given digital display meter, 200 mV in this case, the input signal of the display (68) must be attenuated. A two terminal current sensing resistor (74) is connected across the input terminals of the display (68) to scale the input value to within the value of the display (68). The resistor (74) is preferably a precision +/−1% metal-film resistor, with absolute TCR's (Temperature Coefficient of Resistance) less than 50 ppm/grade Celsius. In the preferred embodiment, the resistor (74) is an Ohmite® two terminal axial resistor having an Ohmic value of 0.050 and having a model number 12FR050. Of course, the type and value of the resistor may be adjusted to obtain any desired scale. By selecting the right value for the resistor (74) a desired maximum value can be displayed on the display (68) when the corresponding potentiometer is turn at max. The max value displayed can be 1999

If a value bigger than 1999 has to be displayed the display will show −1, meaning out of range. In this case a smaller resistance must be used.

The driver (76) is connected to male couplings (78) and (80) which fit into mating engagement with a pair of female couplings (82) and (84). The female couplings (82) and (84) are coupled to a blue light emitting diode (110). Alternatively, the couplings (82) and (84) may be uniquely keyed and color coded to prevent them from being inserted into the incorrect couplings (78) and (80).

In a similar manner, a second double position on/off switch (86) controls power from the voltage regulator (70) to a second three and one half digit LCD/voltmeter (88) and from the inverter (64) to a second light emitting diode driver (90).

Preferably, the second light emitting diode driver (90) is a 350 mA Luxdrive model 03021-D-E-350. A 1 kOhm potentiometer (92) is also coupled to the driver (90). Similarly, a two terminal current sensing resistor (94) is connected across the input terminals of the display (88) to scale the input to within the range of the display (88). The driver (90) is connected to female couplings (96) and (98), which fit into mating engagement with a pair of male couplings (100) and (102). The male couplings (100) and (102) are coupled to a red light emitting diode (114).

Figure 3:
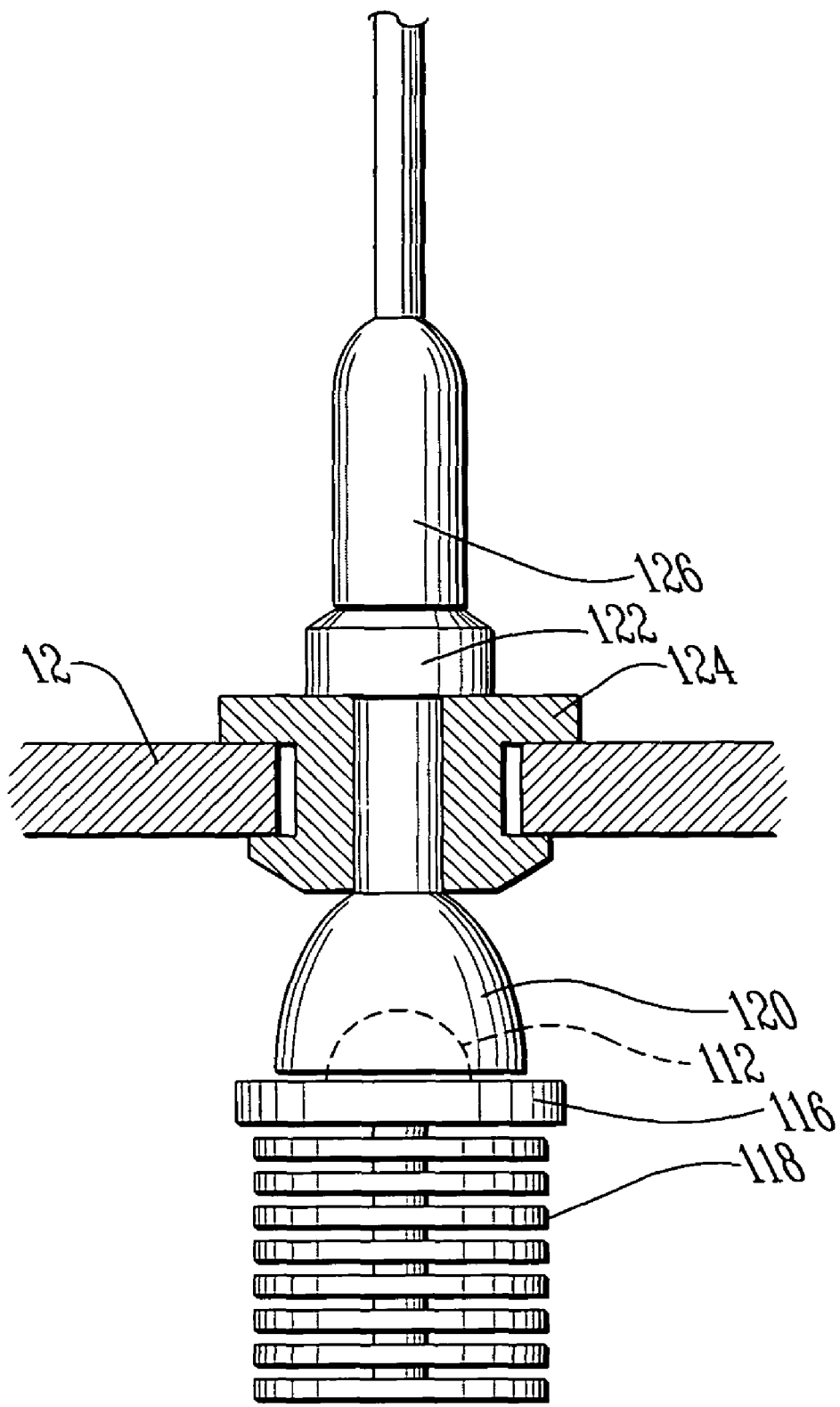
FIG. 3 illustrates a schematic of the white light emitting diode of the present invention;.

Also as shown in FIG. 2 is an on/off switch (104) which controls power from the inverter (64) to a third light emitting diode driver (106). The driver (106) is preferably a 1000 mA driver coupled to a 5 kOhm potentiometer (108). The driver (106) is connected to a white light emitting diode (112). As shown in FIG. 3, the white light emitting diode (112) is coupled using a silicon based thermal compound (116) to a simple heat radiator (118) constructed of aluminum. Provided over the white light emitting diode (112) is a fiber optic light injector (120), focused at a fiber optic cable terminal (122) of a standard light guide (126). A terminal adapter (124) holds the terminal (122) in place. A standard fiber optic cable (126) is coupled to the terminal.

Figure 4:
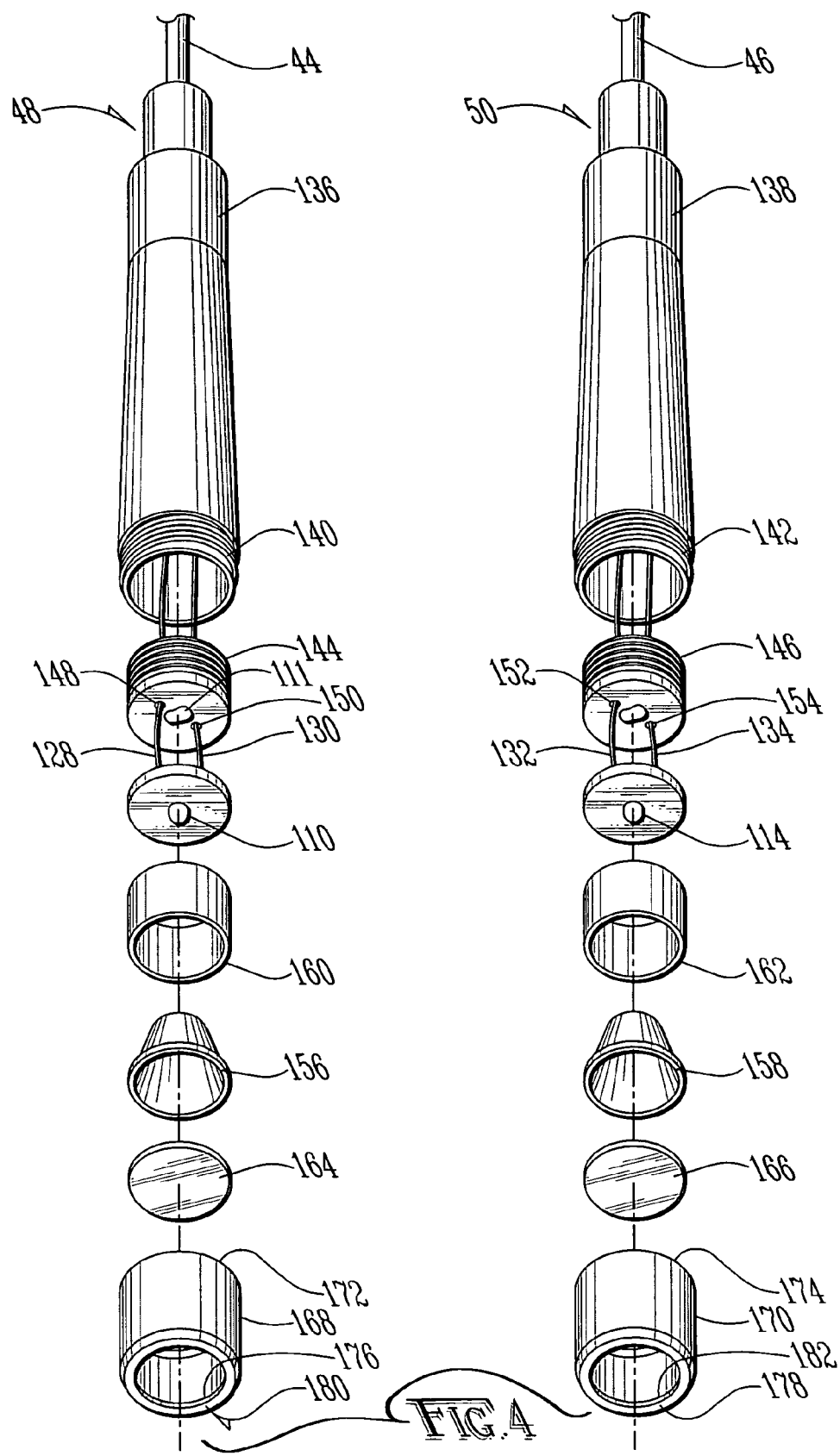
FIG. 4 illustrates an exploded perspective view of the light wands of the diagnostic system of FIG. 1.

As shown in FIG. 4, the light wands (48) and (50) are coupled to the power conduits (44) and (46). Within the light wands (48) and (50) the power conduits (44) and (46) are coupled to wires (128), (130), (132) and (134). While the light wands (48) and (50) maybe constructed of any suitable material, in the preferred embodiment the light wands (48) and (50) are each less than 5 kilograms and, more preferably, each less than 1 kilogram in weight. Handles (136) and (138) of the light wants (48) and (50) are formed from tubular aluminum. Each handle (136) and (138) is provided with threads (140) and (142) near one end, surrounding removable solid cylindrical heat sinks (144) and (146) which transfer heat from the light emitting diodes (110) and (114) to the handles (136) and (138). As shown, the heat sinks (144) and (146) are provided with holes (148), (150), (152) and (154), through which the wires (128), (130), (132) and (134) protrude. The wires (128) and (130) of the blue light wand (48) are coupled to the blue light emitting diode (110).

The blue light emitting diode (110) is connected to the heat sink (144) by a dab of silicone based thermal compound (111). The blue light emitting diode (110) is designed to produce activation of the melanopsin-mediated pupil constriction. The blue light emitting diode (110) may be of any type known in the art, but preferably produces light at a wavelength of between 425 and 525, more preferably between 450 and 500 and, most preferably, about 472 nanometers. In the preferred embodiment the blue light emitting diode (110) is a Blue Lambertian Luxeon® Star light emitting diode LB3C having a bin number of P3KB, having a minimum photometric flux of 23.5 lm and a maximum photometric flux of 30.6 lm, a minimum dominant wavelength of 470 nanometers and a maximum dominant wavelength of 475 nanometers, and a minimum forward voltage of 3.51 and a maximum forward voltage of 3.75. The blue light emitting diode (110) is configured so as to produce a light of an intensity of between 0 kcd/m$^2$ and 1000 kcd/m$^2$, more preferably between 60 kcd/m$^2$ and 300 kcd/m$^2$, even more preferably between 100 kcd/m$^2$ and 250 kcd/m$^2$ and, most preferably, approximately 200 kcd/m$^2$. The blue light emitting diode (110) is also preferably provided to produce at least 50 kcd/m$^2$ more light at 472 nanometers than at 630 nanometers, more preferably at least 100 kcd/m$^2$ more light at 472 nanometers than at 630 nanometers and, most preferably, at least 150 kcd/m$^2$ more light at 472 nanometers than at 630 nanometers. The blue light emitting diode (110) preferably produces at least 50 kcd/m$^2$ more light at a range of wavelengths between 450 and 500 nanometers than at a range of wavelengths between 610 and 650 nanometers.

Similarly, the wires (132) and (134) of the red light wand (50) are coupled to the red light emitting diode (114). The red light emitting diode (114) may be of any type known in the art, but preferably produces light at a wavelength of between 575 and 675, and more preferably between 600 and 650 and, most preferably, about 630 nanometers. The red light emitting diode (114) is configured to activate photoreceptor-mediated component of the pupil light reflex by producing light of an intensity of between 0 kcd/m$^2$ and 1000 kcd/m$^2$, more preferably between 60 kcd/m$^2$ and 300 kcd/m$^2$, even more preferably between 100 kcd/m$^2$ and 250 kcd/m$^2$ and, most preferably, approximately 200 kcd/m$^2$. The red light emitting diode (114) is also preferably provided to produce at least 50 kcd/m$^2$ more light at 630 nanometers than at 472 nanometers, more preferably at least 100 kcd/m$^2$ more light at 630 nanometers than at 472 nanometers and, most preferably, at least 150 kcd/m$^2$ more light at 630 nanometers than at 472 nanometers. The red light emitting diode (114) preferably produces at least 50 kcd/m$^2$ more light at a range of wavelengths between 610 and 650 nanometers than at a range of wavelengths between 450 and 500 nanometers.

In the preferred embodiment the red light emitting diode (114) is a Red Lambertian Luxeon® Star light emitting diode MD1D having a bin number of R4GR identifying a red light emitting diode having a minimum photometric flux of 39.8 lm and a maximum photometric flux of 51.7 lm. The bin number also indicates a maximum dominant wavelength of 620.5 nanometers and a maximum dominant wavelength of 631 nanometers, as well as a minimum forward voltage of 2.79 and a maximum forward voltage of 3.03. Since red light wave length does not overlap with the melanopsin activation spectra, it can not activate the melanopsin-mediated component of the pupil light reflex.

Provided over the light emitting diodes (110) and (114) are collimators (156) and (158) to focus light coming from the light emitting diodes (110) and (114). In the preferred embodiment, the collimators (156) and (158) are Luxeon® Optical Grade Acrylic Plastic Collimator model number XHL-NX05, collimating light into a ten degree beam. The collimators (156) and (158) are preferably provided within optics holders (160) and (162), such as the L$^2$Optics holders designed for the Luxeon® collimators.

Provided over the collimators (156) and (158), are a pair of diffuser discs (164) and (166). The diffuser discs (164) and (166) diffuse the light uniformly to prevent "hot spots." Although the diffuser discs (164) and (166) may be constructed of any suitable material, in the preferred embodiment the diffuser discs (164) and (166) are holographic diffusers constructed of polycarbonate, having a transmission efficiency in excess of eighty-five percent. The holographic diffuser discs (164) and (166) are cut from an unmounted sheet of diffuser material, such as 10° holographic diffuser sheets available from Edmund Optics, having a stock number of NT55-442.

Provided over the diffuser discs (164) and (166) are the light wand caps (168) and (170). As shown in FIG. 4, each cap (168) and (170) is constructed of tubular aluminum provided with interior threads near the bottom (172) and (174) to fit into mating engagement with the threads (140) and (142) of the handles (136) and (138). The caps (168) and (170) are each provided with a circular lip (176) and (178) defining an opening (180) and (182). The lips (176) and (178) retain the diffuser discs (164) and (166), holding the holders (160) and (162) and the collimators (156) and (158) in place over the light emitting diodes (110) and (114) when the caps (178) and (180) are screwed onto the handles (136) and (138).

Figure 5:
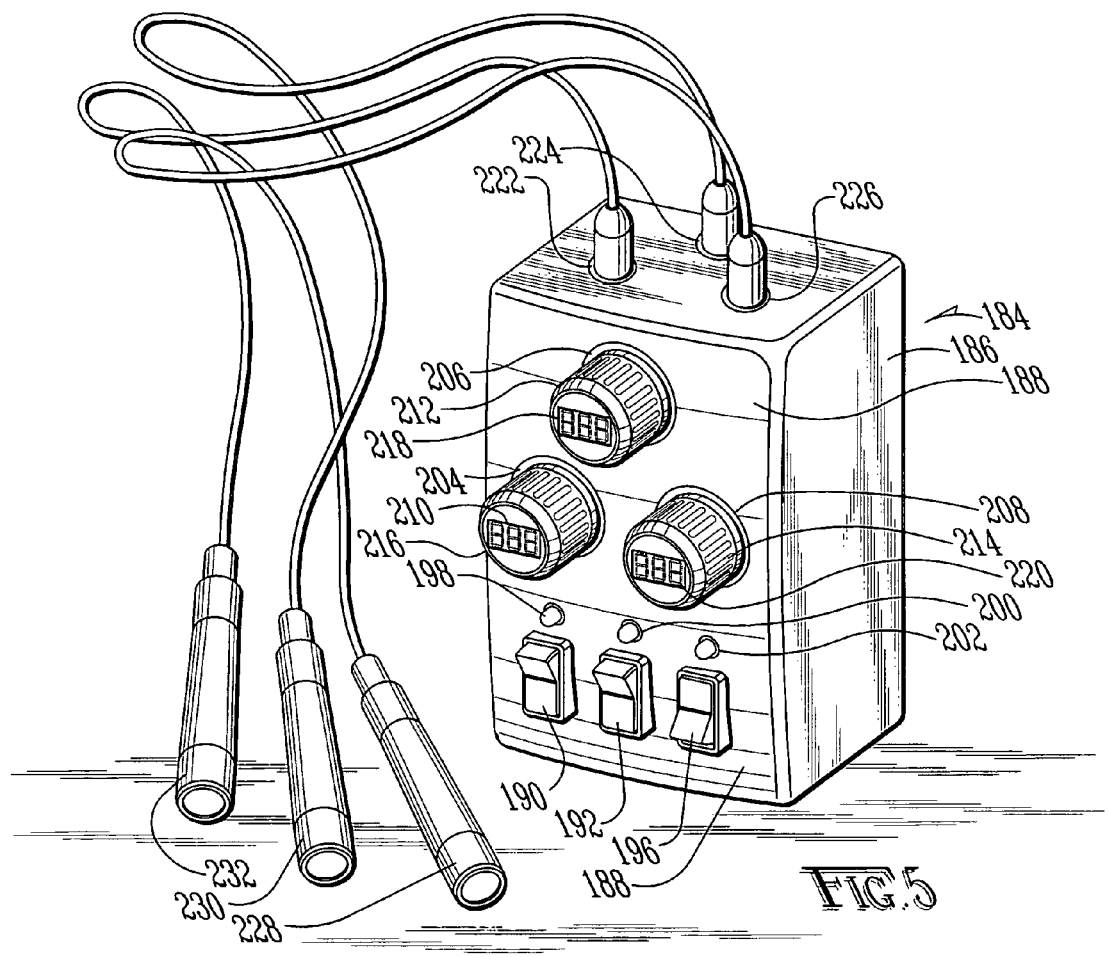
FIG. 5 illustrates a front perspective view of an alternative embodiment of the diagnostic system of the present invention.
Figure 6:
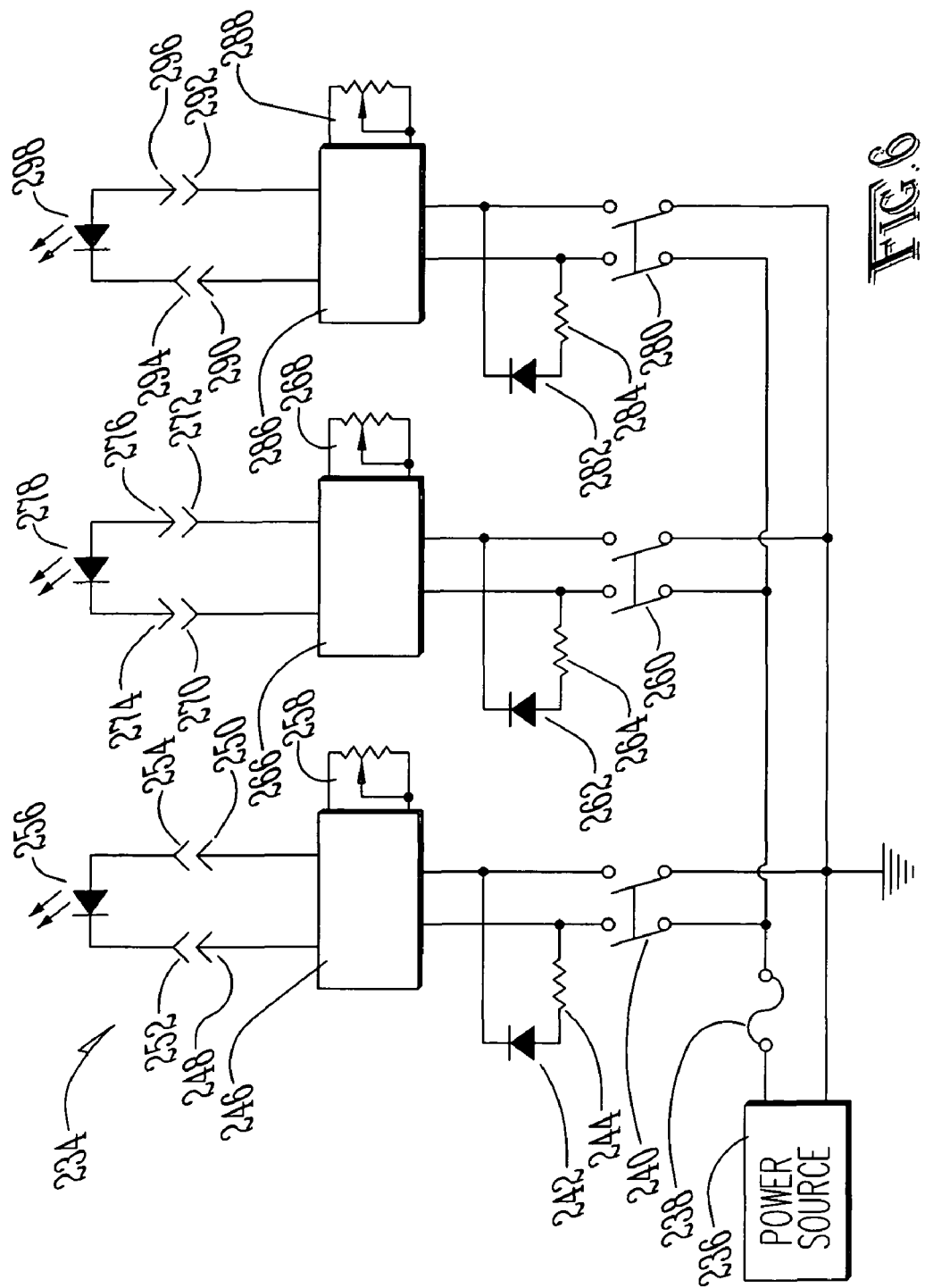
FIG. 6 illustrates a schematic of the electronic components and connections for the alternative embodiment diagnostic system of FIG. 5.

An alternative portable, battery-operated embodiment of the present invention is shown generally as (184) in FIG. 5. The device (184) includes a housing (186), a face (188) provided with three on/off switches (190), (192) and (196), and three light emitting diodes (198), (200) and (202). Provided above each light emitting diode (198), (200) and (202) is a potentiometer (204), (206) and (208). While the potentiometers may be any type known in the art, in the preferred embodiment each potentiometer is a Bourns® 3610S-1-102 10-Turn Precision Knobpot® having a resistance of 1000 ohms with a resolution of 0.035 percent. The potentiometers (204), (206) and (208) are each provided with a mechanical, digital readout (210), (212) and (214), which tracks the movement of dials (216), (218) and (220) of the potentiometers (204), (206) and (208). Also provided on the housing (186) are three outputs (222), (224) and (226), coupled to three light wands (228), (230) and (232). Shown in FIG. 6 is a schematic (234) of the elements provided within the housing (186). (FIGS. 5-6).

The device (184) includes a direct current power supply (236), such as a nine volt battery. Coupled to the power supply is a fuse (238). Also coupled to the power supply (236) is a double position on/off switch (240). The switch (240) is coupled to a small power indicating light emitting diode (242) and a 220 Ohm resistor (244) to limit the power provided through the diode (242). The small LED is used to indicate the device (10) is on. A 700 mA light emitting diode driver (246) is coupled to the switch (240) and, via male couplings (248) and (250) and female couplings (252) and (254), to a blue light emitting diode (256). A 1 kOhm potentiometer (258) is coupled to the driver (246). In a similar manner, a switch (260) couples the power supply (236) to a light emitting diode (262) and resistor (264). The switch (260) is also coupled to a 350 mA light emitting diode driver (266), controlled by a 1 kOhm potentiometer (268). The driver (266) is coupled via female couplings (270) and (272) and male couplings (274) and (276) to a red light emitting diode (278).

If desired, a third switch (280) with light emitting diode (282) and resistor (284) may connect the power supply (236) to a third 350 mA light emitting diode driver (286). The driver is controlled by a 1 kOhm potentiometer (288) and is coupled by male couplings (290) and (294) and female couplings (292) and (296) to a green light emitting diode, preferably providing at least 50 kcd/m² more light at 520 nanometers than at 630 nanometers, more preferably providing at least 100 kcd/m² more light at 520 nanometers than at 630 nanometers, and most preferably providing at least 150 kcd/m² more light at 520 nanometers than at 630 nanometers.

In the preferred embodiment of the present invention, the blue light wand (48) is a source of a blue light with relatively narrow wave length band (480 nm), and an adjustable control of the light output intensities in the range of (0-1000 kcd/m2). The blue light wand (48) is specifically built to achieve the maximal activation of the melanopsin-mediated pupil constriction. The device (10) utilizes the physiological spectral properties of the pupil light reflex. The red light wand (50) has relatively narrow wave length (630 nm—RED light) and an adjustable control of the light output intensities in the range of (0-1000 kcd/m2), which can be specifically used to activate photoreceptor-mediated component of the pupil light reflex. Since red light wave length does not overlap with the melanopsin activation spectra, it can not activate the melanopsin-mediated component of the pupil light reflex.

Figure 7:
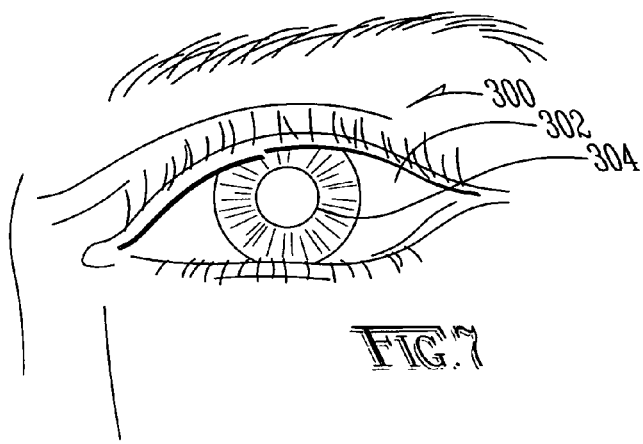
FIG. 7 illustrates an eye with a pupil of normal size.

When it is desired to utilize the device (10) of the present invention, a subject (300) with an eye (302) is presented for testing. As shown in FIG. 4, under normal conditions the pupil (308) of the eye (302) is neither completely dilated nor completely restricted. To begin the test, the switch (14) is actuated to energize the blue light wand (48). (FIGS. 1 and 7). Preferably, the device (10) has been calibrated so that a reading of 100.0 on the digital display (20) translates into a light intensity preferably between 150 kcd/m² and 250 kcd/m², more preferably between 175 kcd/m² and 225 kcd/m² and, most preferably, about 200 kcd/m² of light having a wavelength of preferably between 475 and 485 nanometers and, most preferably, approximately 480 nanometers.

Figure 8:
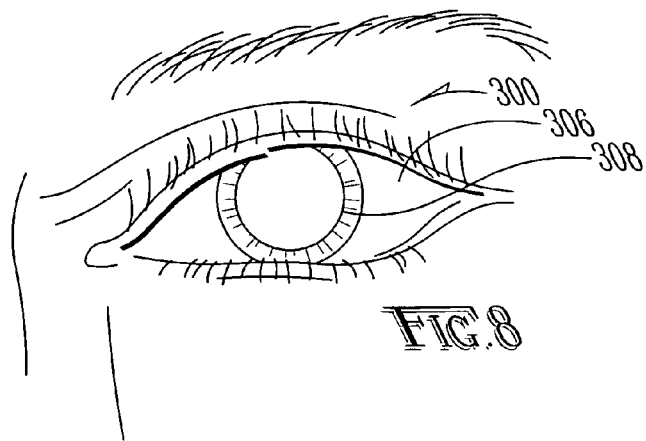
FIG. 8 illustrates the eye of FIG. 4 with the pupil dilated.
Figure 9:
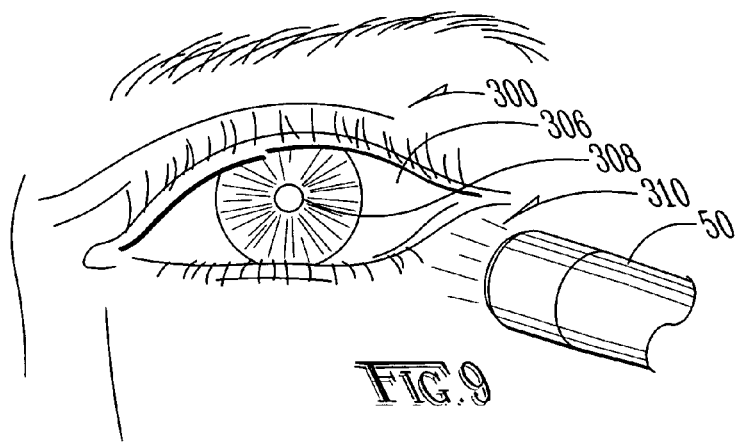
FIG. 9 illustrates the eye of FIG. 4 with the pupil constricted in response to irradiation to blue light.

The subject (300) is then placed in a dark room for approximately thirty seconds, until the pupil (308) dilates as shown in FIG. 8. Thereafter, the blue light wand (48) is positioned approximately 2.5 centimeters from the pupil (308) for approximately five seconds, so as to irradiate the pupil (308) with blue light (310). (FIGS. 1 and 9). The change in the pupil (308) as shown in FIG. 9, with the pupil (308) constricting to a diameter of preferably less than four millimeters is noted. The constriction, or absence thereof, of the pupil (308) is noted. If the pupil (308) constricts to a diameter of less than four millimeters, before five seconds has elapsed, the light wand (50) may be moved away from the eye (306) as soon as the pupil (308) diameter constricts to less than four millimeters.

Figure 10:
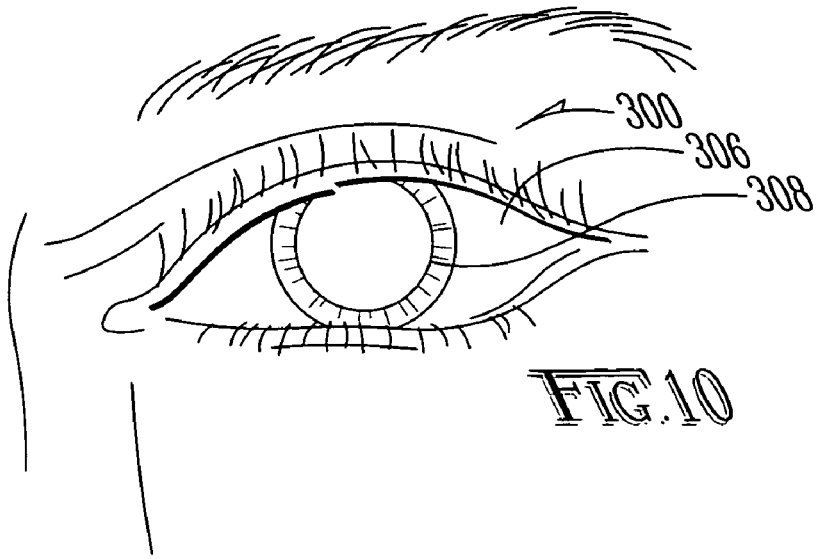
FIG. 10 illustrates the eye of FIG. 4 with the pupil again dilated.

Thereafter, as shown in FIG. 10, the eye (306) is again placed in the dark for thirty seconds so as to dilate the pupil (308). The switch (14) is then flipped so as to turn off the blue light (150) and the switch (15) is actuated to turn on the red light wand (50). The digital readout (30) is previously calibrated to read 100.0 in response to an output of a light intensity preferably between 150 kcd/m² and 250 kcd/m², more preferably between 175 kcd/m² and 225 kcd/m² and, most preferably, about 200 kcd/m² of light having a wavelength of preferably between 625 and 635 nanometers and, most preferably, approximately 630 nanometers.

Figure 11:
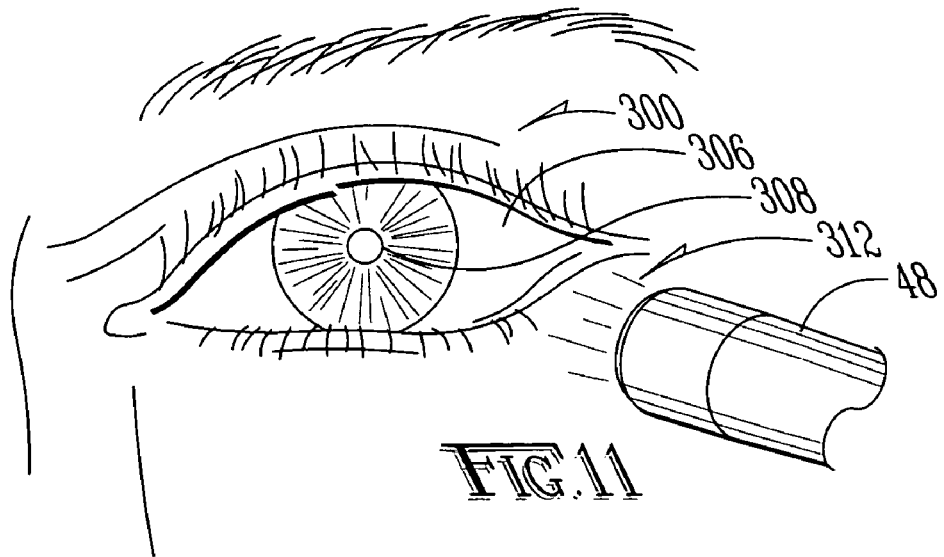
FIG. 11 illustrates the eye of FIG. 4 shown with the pupil constricted in response to irradiation with red light.

As shown in FIG. 11, the red light wand (50) is then moved to within 2.5 centimeters of the pupil (308) for five seconds and any change in the diameter of the pupil (308) is noted. Again, if the pupil (308) constricts to a diameter of less than four millimeters before the five seconds has elapsed, the red light wand (50) emitting the red light (312) is removed from the eye. Thereafter, if it is desired to utilize a different color using a different wavelength adjusted to a particular power, the additional wavelength is applied to the pupil (308) in a similar manner and the results are noted. After all responses have been observed and recorded, the results are utilized in association with other diagnostic parameters to establish a diagnosis.

In patients with retinal photoreceptor disease, activation of the pupil light reflex with a red (312) or green light (~520 nm—not shown) (photoreceptor mediated pathway) will cause completely absent or severely decreased pupil (308) constriction with a frequent presence of the pupillary escape. At the same time, activation of the pupil light reflex with blue light should not cause any detectable deficits at high light intensities, unless inner retina degenerative changes already occurred. The use of lower light intensities for red, green and blue light (at the level of 0-30 kcd/m2) can be utilized to detect very early changes in the photoreceptor function. When patients with optic nerve disease are evaluated, any type of light stimulus (red, green or blue) at the stated intensities will elicit similar pupil light reflex deficits (or absence of the pupil light reflex response) since damage is located at the level of the optic nerve so both components of the PLR (photoreceptor-mediated and melanopsin-mediated) are equally affected. The device (10) can also be utilized to help diagnose immune-mediated retinal diseases. In the cases where red and green response (photoreceptor mediated responses) is absent while blue response (melanopsin-mediated response) is present, and electroretinogram testing shows normal and/or slightly decreased function, immediate diagnosis of immune-mediated retinal disease can be established, since diagnostic findings are suggestive of abnormal synaptic activity within the retina itself. Presence of the central nervous system diseases, which caused cortical blindness, is usually characterized by normal pupil responses to red, green and blue stimuli.

Results obtained with the device (10) are typically combined with clinical observations to diagnose abnormalities. In some situations, such as sudden acquired retinal degeneration, constriction associated with the blue light may be slow and have a delayed onset. Conversely, the red light may not elicit any pupil constriction. This, combined with clinical observations such as the sudden onset of blindness, normal fundus appearance, complete absence of retinal electric activity (no ERKG amplitudes), or slow and delayed pupil light reflex being elicited with very bright light source, may be indicative of retinal degeneration. Similarly, no constrictive response to either the red light or blue light in association with sudden onset of blindness, swollen optic nerve, head appearance on fundus examination or normal retinal electrical activity may be indicative of optic neuritis.

Constrictive response to the blue light and no constrictive response to the red light in association with the sudden onset of blindness, normal fundus appearance, or no other neurological systemic abnormalities, may be indicative of immune medicated retinitis. Similarly, other diagnoses, such as retinal degeneration and retinal detachment may be indicated, depending on pupil constriction in response to the red and blue lights when taken in conjunction with other clinical data.

Although the invention has been described with respect to a preferred embodiment thereof, it is to be understood that it is not to be so limited since changes and modifications can be made therein which are within the full, intended scope of this invention as defined by the appended claims. For example, a third light source may be provided in the green spectrum (wave length at 520 nm). The green light can be used to stimulate green sensitive cones. By using low light intensity stimulus (100 cd/m2 and less) the green light avoids activation of the melanopsin-mediated pupil response. Additionally, a digital camera may be employed to record or to take pictures of the pupil response. A computer with custom software may also be provided to save the data and automatically analyze the percentage change in pupil response. The software may also be used to suggest a diagnosis based on the combined results obtained with the device (10).

What is claimed is:

1. An illumination system comprising:
    (a) a light pen comprising:
        (i) a housing; and
        (ii) a light source comprising:
            a. a light emitting diode source;
            b. wherein said light emitting diode source produces at least 50 kcd/m$^2$ more light at a range of wavelengths between 450 and 500 nanometers than at a range of wavelengths between 610 and 650 nanometers; and
            c. wherein said light emitting diode source produces light at an intensity of at least between 60 kcd/m$^2$ and 350 kcd/m$^2$;
    (b) a supplemental light pen comprising:
        (i) a supplemental housing; and
        (ii) a supplemental light source comprising;
            a. a supplemental light emitting diode source;
            b. wherein said supplemental light emitting giode source produces at least 50 kcd/m$^2$ more light at a range of wavelengths between 610 and 650 nanometers than at a range of wavelengths between 450 and 500 nanometers;
            c. wherein said supplemental light emitting diode source produces light at an intensity of at least between 60 kcd/m$^2$ and 350 kcd/m$^2$;
    (c) wherein said light pen is less than five kilograms in weight; and
    (d) wherein said light pen is less than ten centimeters wide.

2. The illumination system of claim 1, further comprising a supplemental housing provided around said supplemental light emitting diode.

3. The illumination system of claim 1, further comprising a power source coupled to said light emitting diode source and said supplemental light emitting diode source.

4. The illumination system of claim 3, further comprising a potentiometer coupled between said light emitting diode source and said power source.

5. The illumination system of claim 4, further comprising a colluminator provided over said light emitting diode source.

6. The illumination system of claim 5, further comprising a diffuser positioned over said light emitting diode source.

7. The illumination system of claim 4, further comprising a diffuser positioned over said light emitting diode source.

8. An illumination system comprising:
    (a) a first light emitting diode source;
    (b) wherein said first light emitting diode source produces at least 50 kcd/m$^2$ more light at 480 nanometers than at 630 nanometers;
    (c) wherein said first light emitting diode source produces light at an intensity of at least between 60 kcd/m$^2$ and 300 kcd/m$^2$;
    (d) a second light emitting diode source;
    (e) wherein said second light emitting diode source produces at least 50 kcd/m$^2$ more light at 630 nanometers than at 480 nanometers; and
    (f) wherein said second light emitting diode source produces light at an intensity of at least between 60 kcd/m$^2$ and 350 kcd/m$^2$.

9. The illumination system of claim 8, further containing a housing containing said first light emitting diode source and said second light emitting diode source.

10. The illumination system of claim 8, further comprising:
    (a) a first housing containing said first light emitting diode source; and
    (b) a second housing containing said second light emitting diode source.

11. The illumination system of claim 10, further comprising a power source coupled to said first light emitting diode source and said second light emitting diode source.

12. The illumination system of claim 11, further comprising a first flexible power conduit at least ten centimeters long coupling said power source to said first light emitting diode source and a second flexible power cable conduit coupling said power source to said first light emitting diode source.

13. The illumination system of claim 12, further comprising a potentiometer coupled between said first flexible power conduit and said power source.

14. A method for detecting ocular anomalies comprising:
   (a) providing a light emitting diode source;
   (b) wherein said light emitting diode source produces at least 50 kcd/m$^2$ more light at 480 nanometers than at 630 nanometers;
   (c) wherein said light emitting diode source produces light at an intensity of at least between 60 kcd/m$^2$ and 300 kcd/m$^2$;
   (d) providing a pupil;
   (e) dilating a pupil;
   (f) shining a light of an intensity of between 60 kcd/m$^2$ and 300 kcd/m$^2$ at said pupil with said light emitting diode source; and
   (g) analyzing restriction of said pupil in response to light from said light emitting diode source
   (h) providing a supplemental light emitting diode source;
   (i) wherein said supplemental light emitting diode source produces at least 50 kcd/m$^2$ more light at 630 nanometers than at 475 nanometers;
   (j) dilating said pupil;
   (k) shining a light of an intensity of between 60 kcd/m$^2$ and 300 kcd/m$^2$ at said pupil with said supplemental light emitting diode source; and
   (l) analyzing restriction of said pupil in response to light from said supplemental light emitting diode source.

15. The method of detecting ocular anomalies of claim 14, further comprising:
   (a) providing a potentiometer; and
   (b) coupling said potentiometer between said power source and said light emitting diode source.

16. The method of detecting ocular anomalies of claim 14, wherein at least eighty percent of light produced by said supplemental light emitting diode source is within 20 nanometers of 630 nanometers.

17. The method of detecting ocular anomalies of claim 16, wherein at least eighty percent of light produced by said light emitting diode source is within 20 nanometers of 475 nanometers.

18. The method of detecting ocular anomalies of claim 14, wherein at least eighty percent of light produced by said light emitting diode source is within 20 nanometers of 475 nanometers.

* * * * *